US012141503B1

(12) United States Patent
Chhugani et al.

(10) Patent No.: US 12,141,503 B1
(45) Date of Patent: *Nov. 12, 2024

(54) SYSTEMS AND METHODS TO IMPLEMENT COMMANDS BASED ON SELECTION SEQUENCES TO A USER INTERFACE

(71) Applicant: Suki AI, Inc., Redwood City, CA (US)

(72) Inventors: Jatin Chhugani, Mountain View, CA (US); Ganesh Satish Mallya, Santa Clara, CA (US); Alan Diec, Sunnyvale, CA (US); Vamsi Reddy Chagari, Milpitas, CA (US); Sudheer Tumu, Santa Clara, CA (US); Nithyanand Kota, Santa Clara, CA (US); Maneesh Dewan, Sunnyvale, CA (US)

(73) Assignee: Suki AI, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/522,214

(22) Filed: Nov. 28, 2023

Related U.S. Application Data (63) Continuation of application No. 18/184,535, filed on Mar. 15, 2023, now Pat. No. 11,853,652, which is a continuation of application No. 17/224,042, filed on Apr. 6, 2021, now Pat. No. 11,614,917.

(51) Int. Cl.
*G10L 15/22* (2006.01)
*G06F 3/16* (2006.01)
*G10L 15/08* (2006.01)

(52) U.S. Cl.
CPC .............. *G06F 3/167* (2013.01); *G10L 15/08* (2013.01); *G10L 15/22* (2013.01); *G10L 2015/088* (2013.01)

(58) Field of Classification Search
CPC .......... G06F 3/167; G10L 15/08; G10L 15/22
See application file for complete search history.

(56) References Cited

U.S. PATENT DOCUMENTS

| 11,508,373 B1 | 11/2022 | Dewan | |
|---|---|---|---|
| 11,614,917 B1* | 3/2023 | Chhugani | ............... G06N 20/00 |
| | | | 715/728 |
| 2009/0172546 A1* | 7/2009 | Chang | ..................... G06F 3/167 |
| | | | 715/728 |
| 2020/0293167 A1* | 9/2020 | Blyumen | .............. G06F 16/904 |

* cited by examiner

*Primary Examiner* — Ibrahim Siddo
(74) *Attorney, Agent, or Firm* — Esplin & Associates, PC (57) ABSTRACT

Systems and methods to implement commands based on selection sequences to a user interface are disclosed. Exemplary implementations may: store, electronic storage, a library of terms utterable by users that facilitate implementation of intended results; obtain audio information representing sounds captured by a client computing platform; detect the spoken terms uttered by the user present within the audio information; determine whether the spoken terms detected are included in the library of terms; responsive to determination that the spoken terms are not included in the library of terms, effectuate presentation of an error message via the user interface; record a selection sequence that the user performs subsequent to the presentation of the error message that causes a result; correlate the selection sequence with the spoken terms based on the selection sequence recorded subsequent to error message to generate correlation; and store the correlation to the electronic storage.

18 Claims, 4 Drawing Sheets

SYSTEMS AND METHODS TO IMPLEMENT COMMANDS BASED ON SELECTION SEQUENCES TO A USER INTERFACE

FIELD OF THE DISCLOSURE

The present disclosure relates to systems and methods to implement commands based on selection sequences to a user interface.

BACKGROUND

Determining a result to cause in response to a command spoken by a user may be a known technique to execute spoken commands. However, such technique limits how many spoken commands are executable by the user to merely commands that are contemplated and stored.

SUMMARY

One aspect of the present disclosure relates to a system enabling implementation of any command given that operations to execute a command are the same amongst users of the system. Multiple users may utter spoken terms (which are captured by client computing platforms) that may comprise a command executable to attain an intended result. Upon the system determining that the command is not currently supported (i.e., the command cannot be executed), the users may be presented with an error message via a user interface of their client computing platforms. The error message may prompt the users to manually execute the command so that the users select particular user interface elements (e.g., virtual buttons presented via the user interface) to attain the intended result. The system may record the selections and correlate those selections with the spoken terms. The correlation may be stored so that upon other users uttering the same spoken terms, the selections may be performed and therefore the command may be executed to obtain the intended result. As such, commands supported by the system may expand based on frequency of utterance of the spoken terms and the same subsequent selections to the user interface elements thereby eliminate users or administrators to manual define commands that the system supports. Such system may facilitate execution and support of infinite commands.

One aspect of the present disclosure relates to a system configured to implement commands based on selection sequences to a user interface. The system may include one or more hardware processors configured by machine-readable instructions, electronic storage, and/or other components. Instruction components may include one or more of analysis component, term determination component, error message effectuation component, selection sequence recording component, correlation component, and/or other instruction components.

The electronic storage may be configured to store a library of terms utterable by users that facilitate implementation of intended results. The terms correspond to commands that may be executable to attain the intended results.

The analysis component may be configured to obtain audio information representing sounds captured by a client computing platform. The sounds include spoken terms uttered by a user. The client computing platform may present a user interface including user interface elements that facilitate selection and/or entry of input. The analysis component may be configured to analyze the sounds captured by the client computing platform to detect any spoken terms uttered by the user present within the audio information.

The term determination component may be configured to determine whether any of the detected spoken terms are included in the library of terms. The determination may be responsive to detection of one or more spoken terms.

The error message effectuation component may be configured to, responsive to determination that at least one of the detected spoken terms are not included in the library of terms, effectuate presentation of an error message via the user interface.

The selection sequence recording component may be configured to record a selection sequence that the user performs subsequent to the presentation of the error message that causes an intended result.

The correlation component may be configured to correlate the selection sequence with the spoken terms based on the selection sequence recorded subsequent to error message to generate correlation. The correlation component may be configured to store the correlation to the electronic storage.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
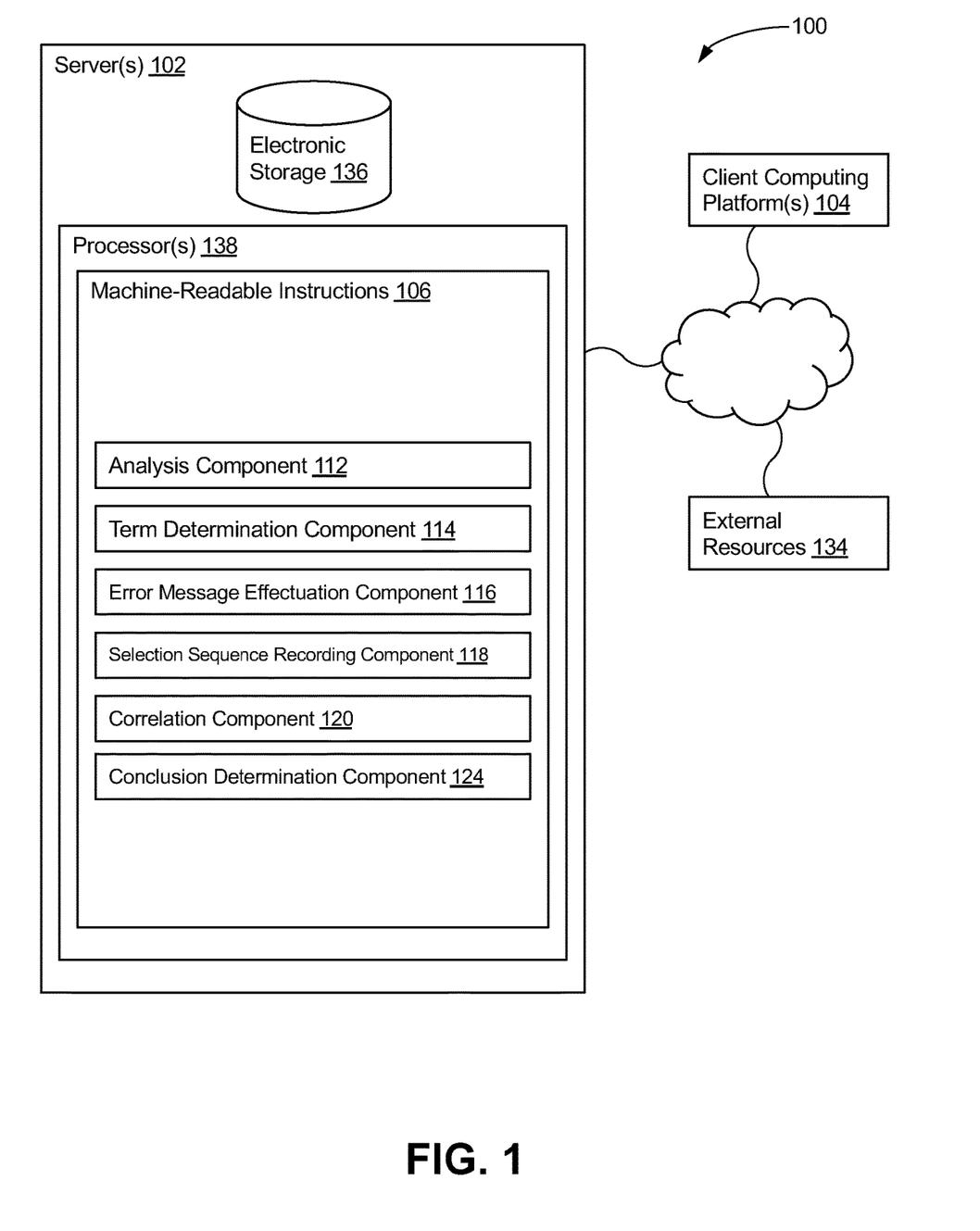
FIG. 1 illustrates a system configured to implement commands based on selection sequences to a user interface, in accordance with one or more implementations.

FIG. 1 illustrates a system 100 configured to implement commands based on selection sequences to a user interface, in accordance with one or more implementations. In some implementations, system 100 may include one or more servers 102. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104. The present disclosure is related to co-pending application Ser. No. 17/221,603 entitled "SYSTEMS AND METHODS TO TRANSLATE A SPOKEN COMMAND TO A SELECTION SEQUENCE", the contents of which are incorporated herein by reference in its entirety.

Individual client computing platforms 104 may be associated with individual users. For example, users may include a doctor, a nurse, a physician, an authorized medical personnel, a clinician, a caregiver, and/or other users. Client computing platform 104 may present a user interface including user interface elements that facilitate selection and/or entry of input. The user interface elements may be configured to facilitate user interaction with the user interface, user entry, and/or selection. By way of non-limiting illustration, the user interface elements may include one or more of text input fields, drop down menus, check boxes, display windows, virtual buttons, virtual keys to a virtual keyboard and virtual keypad, and/or other user interface elements.

Electronic storage 136 may be configured to store a library of terms utterable by users that facilitate implementation of intended results. The terms may correspond to commands that are executable to attain the intended results. An intended result may refer to an outcome requested and spoken by the user (e.g., one of the commands). By way of non-limiting illustration, a result may be presentation of a particular note for a particular patient, modifications to a particular note, modifications to an appointment, or other results. Results described herein are for illustrative purposes and are not intended to be limiting. Thus, upon utterance of particular ones of the terms included in the library, a corresponding command may be executed. Executing the command may include a selection sequence, speech recognition performance, retrieval of particular information (e.g., a note for a patient) based on the speech recognition, and/or other operations that execute the command to attain the intended result.

Server(s) 102 may be configured by machine-readable instructions 106. Machine-readable instructions 106 may include one or more instruction components. The instruction components may include computer program components. The instruction components may include one or more of analysis component 112, term determination component 114, error message effectuation component 116, selection sequence recording component 118, correlation component 120, conclusion determination component 124, and/or other instruction components.

Analysis component 112 may be configured to obtain audio information representing sounds captured by client computing platform 104. Analysis component 112 may be configured to analyze the sounds captured by client computing platform 104 to detect any spoken terms uttered by the user present within the audio information. The spoken terms may be terms that the user has spoken, and thus have been captured and represented as the audio information. In some implementations, at least some of the spoken terms uttered by the user may comprise one of the commands that correspond with terms included in the library of terms that cause the intended results. In some implementations, some of the spoken terms may comprise a command not yet corresponding with terms included in the library of terms. In some implementations, analyzing the spoken terms may include performance of speech recognition techniques, other novel techniques, and/or other known techniques for detecting the spoken terms. In some implementations, analysis component 112 may be configured to determine a total amount of detected spoken terms. The total amount of detected spoken terms may indicate how many spoken terms have been detected.

Term determination component 114 may be configured to determine whether any of the detected spoken terms are included in the library of terms. The determination may be responsive to the detection of one or more spoken terms. The determination may indicate whether the detected spoken terms the user uttered (i.e., a sort of command) comprise/is currently a command that system 100, or a system in conjunction with system 100, may execute given the correspondences stored between the terms and command, correlations, and/or other information in electronic storage 136. In some implementations, term determination component 114 may be configured to determine an amount of the detected spoken terms that are included in the library. For example, the detected spoken terms may include a first term, a second term, and a third term where two of the detected spoken terms, the first term and the second term, are determined to be included in the library. In some implementations, term determination component 114 may be configured to compare the total amount of detected spoken terms with the amount of the detected spoken terms that are included in the library to determine whether the amount of the detected spoken terms that are included in the library is less than the total amount of detected spoken terms. In some implementations, term determination component 114 may be configured to determine how much the amount of the detected spoken terms that are included in the library is less than the total amount based on the comparison.

Error message effectuation component 116 may be configured to effectuate presentation of an error message via the user interface. Effectuation of presentation of the error message may be responsive to determination that at least one of the detected spoken terms are not included in the library of terms. In some implementations, effectuation of presentation of the error message may be based on term determination component 114 determining that the amount of the detected spoken terms that are included in the library is less than the total amount of detected spoken terms indicating that at least one of the detected spoken terms is not included in the library of terms. For example, the total amount of detected spoken terms may be three and two (the first term and the second term) of the detected spoken terms may be included in the library. Thus, the presentation of the error message may be effectuated.

In some implementations, effectuation of presentation of the error message may be responsive to determination that the amount of the detected spoken terms that are included in the library is less than a specific amount relative to the total amount. The specific amount may be a specific number (e.g., 5), a percentage, a ratio, or other specific amount. For example, a total amount of the detected spoken terms may be ten (i.e., ten spoken terms have been detected based on the sounds). Upon the amount of the detected spoken terms that are included in the library being less than 80% the total amount of the detected spoken terms, the presentation of the error message may be effectuated. Seven of the detected spoken terms may be determined as included in the library. Therefore, the error message may be presented since the seven detected spoken terms that are included in the library is less than 80% of the total amount.

The error message may convey to the user that the spoken terms as the sort of command is not executable (i.e., the spoken terms do not correspond with a command that is executable) by system 100. For example, the error message may state "Command not supported" or variations thereof. The error message may indicate to the user to subsequently perform operations manually that attain their intended result. The operations may include a selection sequence and/or other operations.

Selection sequence recording component 118 may be configured to record the selection sequence that the user performs subsequent to the presentation of the error message that causes a result. The selection sequence may represent selections of the user interface elements that cause the intended result. The selections of the user interface elements may be of particular user interface elements and in a particular order. By way of non-limiting illustration, the selection sequence may include selection of a first user interface element, followed by selection of second user interface element, and followed by selection of third user interface element to execute the command. The user interface elements included and presented via the user interface may include the first user interface element, the second user interface element, the third user interface element, and/or other user interface elements. Recording of the selection sequence may include temporarily storing, to electronic storage 136, the selections as individual selections occur.

In some implementations, conclusion determination component 124 may be configured to determine conclusion of the selection sequence to conclude the recording of the selection sequence. In some implementations, the selection sequence may be considered concluded upon a particular amount of time passing since the selection to the user interface elements. For example, the particular amount of time passing since the selection to the user interface elements may be 10 seconds, 15 seconds, or other amount of time.

In some implementations, the user interface may include a conclusion button. The conclusion button may be a particular user interface element that represents conclusion of the selection sequence. The selection sequence may be considered concluded upon selection of the conclusion button. Conclusion determination component 124 may be configured to obtain an indication of the selection of the conclusion button from client computing platform 104. Thus, determining the conclusion of the selection sequence to conclude the recording may be responsive to determining selection of the conclusion button.

Correlation component 120 may be configured to correlate the selection sequence with the spoken terms based on the selection sequence recorded subsequent to error message to generate a correlation. In some implementations, the correlating of the selection sequence with the spoken terms may be responsive to the determination of conclusion of the selection sequence. The correlating may be based on unsupervised clustering, outlier removal, a particular frequency of occurrence of the selection sequence subsequent to the detection of the spoken terms, other known correlation techniques, and/or other information. That is, upon a plurality of various or the same selection sequences recording subsequent to the spoken terms, the selection sequence may be correlated with the spoken terms.

In some implementations, correlation component 120 may be configured to determine frequency of the selection sequence performed by the users subsequent to obtainment of other audio information representing sounds that include the spoken terms uttered by other users and subsequent to presentation of the error message. Thus, correlating the selection sequence and the spoken terms to generate the correlation may be responsive to the frequency meeting a frequency threshold. The frequency threshold may be definable or fixed by system 100. The frequency threshold may be defined by the users, an administrative user, a supervisory user, and/or other users. The frequency threshold may be a specific amount, a percentage, a ratio, or other amount that upon attainment, the spoken terms and the selection sequence are correlated. For example, upon the spoken terms (and presentation of the error message) and subsequently recording the same selection sequence (via selection sequence recording component 118) occurring 100 times, the spoken terms may be correlated with the selection sequence given that the frequency threshold is 75. Correlation component 120 may be configured to store the correlations determined to electronic storage 136. Thus, upon the selection sequence occurring enough subsequent to utterance the spoken terms (e.g., based on attaining the frequency threshold, unsupervised clustering, outlier removal, etc.), the selection sequence may be correlated with the preceding spoken terms uttered by the users. As such, upon the users subsequently uttering these same spoken terms, the selection sequence be may performed (i.e., execute a command now supported by system 100). The users or administrative users may not be required to define spoken terms that execute commands nor how the commands are executed.

By way of non-limiting illustration, in some implementations, analysis component 112 may be configured to obtain secondary audio information representing other sounds captured by client computing platform 104. Client computing platform 104 may be the same as client computing platform 104 that captured the audio information. In some implementations, client computing platform 104 may be different that the one that captured the audio information though communicative with server(s) 102. The other sounds may include the spoken terms uttered by a second user. Analysis component 112 may be configured to detect the spoken terms uttered by the second user present within the secondary audio information. Term determination component 114 may be configured to determine whether the spoken terms uttered by the second user are similar to or the same as the spoken terms included in the library of terms and correlated with the selection sequence.

In some implementations, term determination component 114 may be configured to obtain the correlation from the electronic storage 136 based on the spoken terms and responsive to determination that the spoken terms uttered by second user are the same as the spoken terms included in the library of terms and correlated with the selection sequence. As such, term determination component 114 may be configured to perform, based on the correlation, the selection sequence correlated with the spoken terms to execute a command and cause the intended result.

Figure 3A:
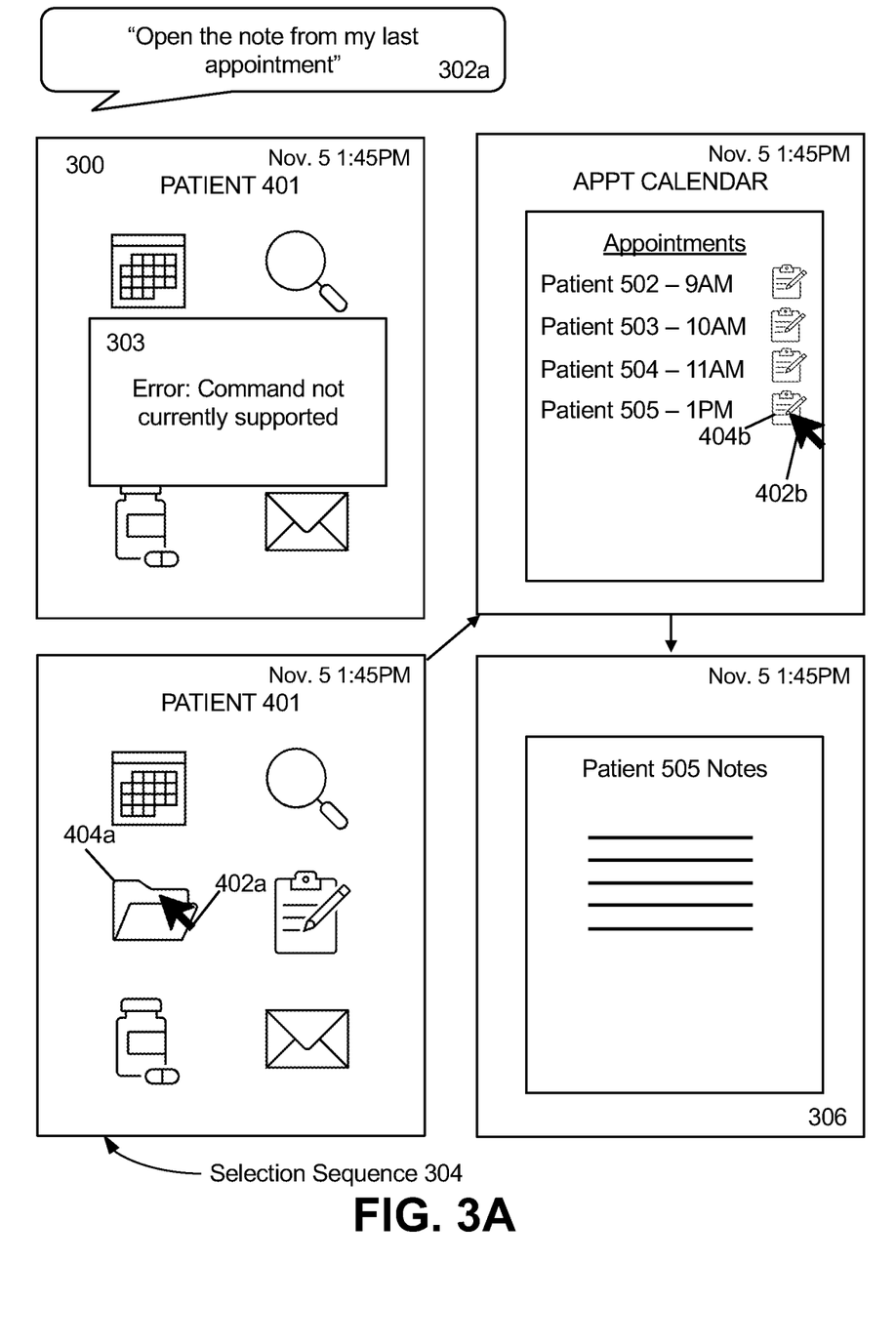
FIG. 3A-B illustrate example implementations, in accordance with one or more implementations.

FIG. 3A-B illustrates an example implementation, in accordance with one or more implementations. FIG. 3A illustrates spoken terms 302a that a user may utter. Upon system 100 (from FIG. 1) detecting the spoken terms and determining that at least one of the spoken terms is not included in the library of terms that correspond with commands that are executable to attain results, presentation of an error message 303 may be effectuated via a user interface 300. Error message 303 may prompt the user to perform a selection sequence 304. Selection sequence 304 may include selection 402a of contextual user interface element 404a (e.g., a folder button) and selection 402b of user interface element 404b (e.g., the last appointment note for patient 505). Selection sequence 304 may cause intended result 306 (e.g., note from the last appointment).

Figure 3B:
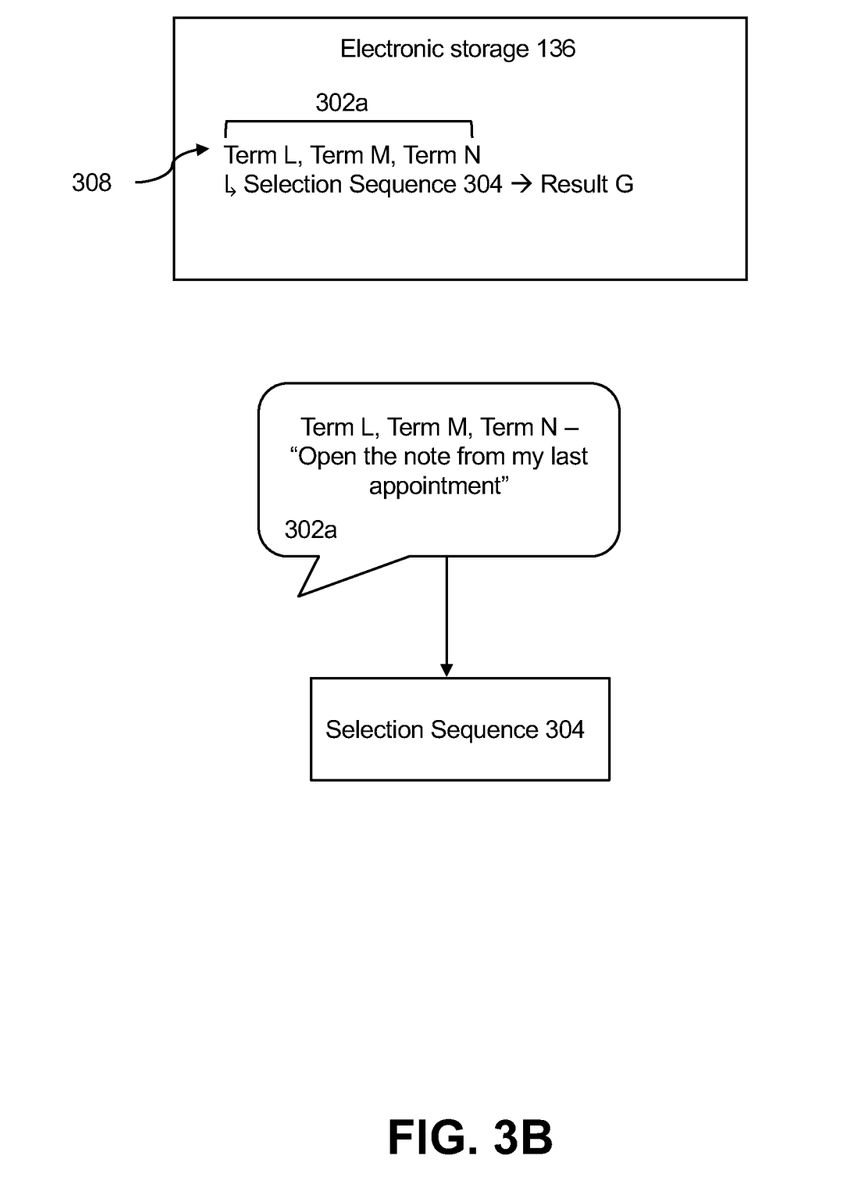

FIG. 3B illustrates electronic storage 136, the same as FIG. 1. Spoken terms 302a (e.g., Term L, Term M, and Term N of spoken terms 302a) may be correlated with selection sequence 304 of FIG. 3A that cause a result G (i.e., the last appointment note for a patient), such as the last appointment note related to patient 505 of FIG. 3A, as a correlation 308. Thus, upon the user or other users uttering spoken terms 302a, selection sequence 304 may be determined based on spoken terms 302a and correlation 308 and performed to cause result G.

In some implementations, server(s) 102, client computing platform(s) 104, and/or external resources 134 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 134 may be operatively linked via some other communication media.

A given client computing platform 104 may include one or more processors configured to execute computer program components. The computer program components may be configured to enable an expert or user associated with the given client computing platform 104 to interface with system 100 and/or external resources 134, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 134 may include sources of information outside of system 100, external entities participating with system 100, and/or other resources. In some implementations, some or all of the functionality attributed herein to external resources 134 may be provided by resources included in system 100.

Server(s) 102 may include electronic storage 136, one or more processors 138, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 136 may comprise non-transitory storage media that electronically stores information. The electronic storage media of electronic storage 136 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 136 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 136 may include one or more virtual storage resources (e.g., cloud storage, a virtual private network, and/or other virtual storage resources). Electronic storage 136 may store software algorithms, information determined by processor(s) 138, information received from server(s) 102, information received from client computing platform(s) 104, and/or other information that enables server(s) 102 to function as described herein.

Processor(s) 138 may be configured to provide information processing capabilities in server(s) 102. As such, processor(s) 138 may include one or more of a digital processor, an analog processor, a digital circuit designed to process information, an analog circuit designed to process information, a state machine, and/or other mechanisms for electronically processing information. Although processor(s) 138 is shown in FIG. 1 as a single entity, this is for illustrative purposes only. In some implementations, processor(s) 138 may include a plurality of processing units. These processing units may be physically located within the same device, or processor(s) 138 may represent processing functionality of a plurality of devices operating in coordination. Processor(s) 138 may be configured to execute components 112, 114, 116, 118, 120, and/or 124, and/or other components. Processor(s) 138 may be configured to execute components 112, 114, 116, 118, 120, and/or 124, and/or other components by software; hardware; firmware; some combination of software, hardware, and/or firmware; and/or other mechanisms for configuring processing capabilities on processor(s) 138. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 112, 114, 116, 118, 120, and/or 124 are illustrated in FIG. 1 as being implemented within a single processing unit, in implementations in which processor(s) 138 includes multiple processing units, one or more of components 112, 114, 116, 118, 120, and/or 124 may be implemented remotely from the other components. The description of the functionality provided by the different components 112, 114, 116, 118, 120, and/or 124 described below is for illustrative purposes, and is not intended to be limiting, as any of components 112, 114, 116, 118, 120, and/or 124 may provide more or less functionality than is described. For example, one or more of components 112, 114, 116, 118, 120, and/or 124 may be eliminated, and some or all of its functionality may be provided by other ones of components 112, 114, 116, 118, 120, and/or 124. As another example, processor(s) 138 may be configured to execute one or more additional components that may perform some or all of the functionality attributed below to one of components 112, 114, 116, 118, 120, and/or 124.

Figure 2:
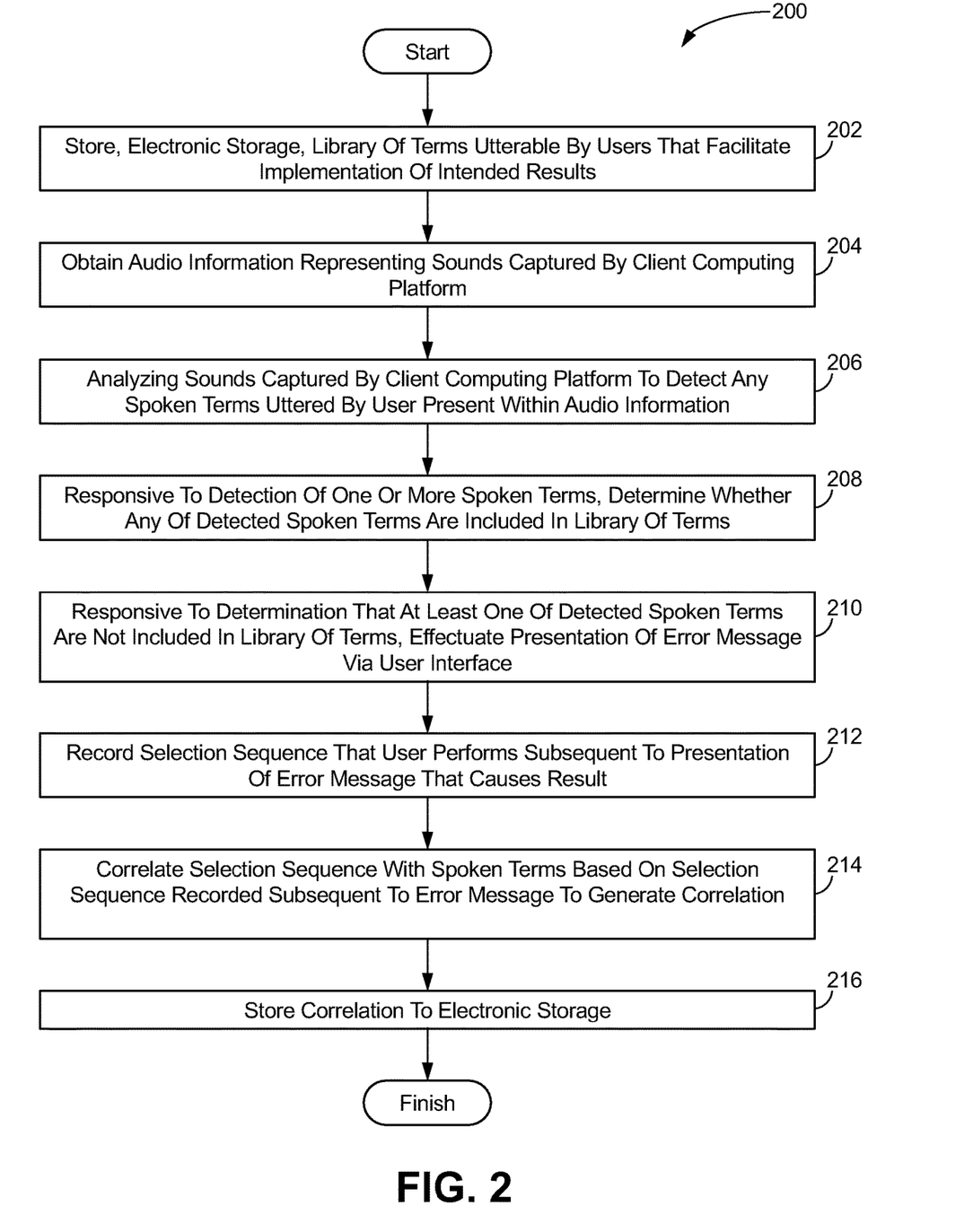
FIG. 2 illustrates a method to implement commands based on selection sequences to a user interface, in accordance with one or more implementations.

FIG. 2 illustrates a method 200 to implement commands based on selection sequences to a user interface, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include storing, electronic storage, a library of terms utterable by users that facilitate implementation of intended results. The terms correspond to sets of commands that may be executable to attain the intended results. Operation 202 may be performed by electronic storage 136, in accordance with one or more implementations.

An operation 204 may include obtaining audio information representing sounds captured by a client computing platform. The client computing platform may present a user interface including user interface elements that facilitate selection and/or entry of input. Operation 204 may be performed by one or more hardware processors configured by machine-readable instructions including a component that is the same as or similar to analysis component 112, in accordance with one or more implementations. An operation 206 may include analyzing the sounds captured by the client computing platform to detect any spoken terms uttered by the user present within the audio information. Operation 206 may be performed by one or more hardware processors configured by machine-readable instructions including a component that is the same as or similar to analysis component 112, in accordance with one or more implementations.

An operation 208 may include responsive to detection of one or more spoken terms, determining whether any of the detected spoken terms are included in the library of terms. Operation 208 may be performed by one or more hardware processors configured by machine-readable instructions including a component that is the same as or similar to term determination component 114, in accordance with one or more implementations.

An operation 210 may include responsive to determination that at least one of the detected spoken terms are not included in the library of terms, effectuating presentation of an error message via the user interface. Operation 210 may be performed by one or more hardware processors configured by machine-readable instructions including a component that is the same as or similar to error message effectuation component 116, in accordance with one or more implementations.

An operation 212 may include recording a selection sequence that the user performs subsequent to the presentation of the error message that causes a result. Operation 212 may be performed by one or more hardware processors configured by machine-readable instructions including a component that is the same as or similar to selection sequence recording component 118, in accordance with one or more implementations.

An operation 214 may include correlating the selection sequence with the spoken terms based on the selection sequence recorded subsequent to error message to generate correlation. Operation 214 may be performed by one or more hardware processors configured by machine-readable instructions including a component that is the same as or similar to correlation component 120, in accordance with one or more implementations.

An operation 216 may include storing the correlation to the electronic storage. Operation 216 may be performed by one or more hardware processors configured by machine-readable instructions including a component that is the same as or similar to correlation component 120, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to implement commands based on selection sequences to a user interface, the system comprising:
   electronic storage configured to store a library of terms utterable by users that facilitate implementation of intended results, wherein the terms correspond to commands that are executable to attain the intended results; and
   one or more processors configured by machine-readable instructions to:
      obtain audio information representing sounds captured by a client computing platform, wherein the client computing platform presents a user interface including user interface elements that facilitate selection and/or entry of input;
      detect any spoken terms uttered by the user present within the audio information;
      determine whether the detected spoken terms are included in the library of terms;
      determine, based on an amount of the detected spoken terms, whether to cause the user interface to enable the user to perform a selection sequence that causes an intended result;
      record the selection sequence that the user performs;
      correlate the selection sequence with the spoken terms based on the selection sequence recorded subsequent to error message to generate a correlation; and
      store the correlation to the electronic storage.

2. The system of claim 1, wherein the one or more processors are further configured by the machine-readable instructions to:
   determine conclusion of the selection sequence to conclude the recording of the selection sequence.

3. The system of claim 2, wherein the user interface includes a conclusion button, wherein the one or more processors are further configured by the machine-readable instructions to:
   obtain an indication of selection of the conclusion button from the client computing platform, wherein determining the conclusion of the selection sequence to conclude the recording is responsive to determining selection of the conclusion button.

4. The system of claim 1, wherein the one or more processors are further configured by the machine-readable instructions to:
   obtain secondary audio information representing other sounds captured by the client computing platform, wherein the other sounds comprise the spoken terms uttered by a second user;
   detect the spoken terms uttered by the second user present within the secondary audio information;

determine whether the spoken terms uttered by the second user are similar to or the same as the spoken terms included in the library of terms and correlated with the selection sequence;

obtain the correlation from the electronic storage based on the spoken terms and responsive to determination that the spoken terms uttered by second user are the same as the spoken terms included in the library of terms and correlated with the selection sequence; and perform, based on the correlation, the selection sequence correlated with the spoken terms to execute a command and cause the intended result.

5. The system of claim 1, wherein the one or more processors are further configured by the machine-readable instructions to:

determine frequency of the selection sequence performed by the users subsequent to obtainment of other audio information representing sounds that comprise the spoken terms uttered by other users and subsequent to presentation of the error message, wherein correlating the selection sequence and the terms to generate the correlation is responsive to the frequency meeting a frequency threshold.

6. The system of claim 5, wherein the frequency threshold is definable or fixed by the system.

7. The system of claim 1, wherein the correlating is based on unsupervised clustering.

8. The system of claim 1, wherein the correlating is based on outlier removal.

9. The system of claim 1, wherein the selection sequence represents selections of user interface elements that cause the intended result such that the selection sequence includes selection of a first user interface element, followed by selection of second user interface element, and followed by selection of third user interface element to execute the command, wherein the user interface elements include the first user interface element, the second user interface element, and the third user interface element.

10. A method configured to implement commands based on selection sequences to a user interface, the method comprising:

storing, in electronic storage, a library of terms utterable by users that facilitate implementation of intended results, wherein the terms correspond to commands that are executable to attain the intended results;

obtaining audio information representing sounds captured by a client computing platform, wherein the client computing platform presents a user interface including user interface elements that facilitate selection and/or entry of input;

detecting any spoken terms uttered by the user present within the audio information;

determining whether the detected spoken terms are included in the library of terms;

determining, based on an amount of the detected spoken terms, whether to cause the user interface to enable the user to perform a selection sequence that causes an intended result;

recording the selection sequence that the user performs;

correlating the selection sequence with the spoken terms based on the selection sequence recorded subsequent to error message to generate a correlation; and storing the correlation to the electronic storage.

11. The method of claim 10, further comprising:

determine conclusion of the selection sequence to conclude the recording of the selection sequence.

12. The method of claim 11, wherein the user interface includes a conclusion button, further comprising:

obtaining an indication of selection of the conclusion button from the client computing platform, wherein determining the conclusion of the selection sequence to conclude the recording is responsive to determining selection of the conclusion button.

13. The method of claim 10, further comprising:

obtaining secondary audio information representing other sounds captured by the client computing platform, wherein the other sounds comprise the spoken terms uttered by a second user;

detecting the spoken terms uttered by the second user present within the secondary audio information;

determining whether the spoken terms uttered by the second user are similar to or the same as the spoken terms included in the library of terms and correlated with the selection sequence;

obtaining the correlation from the electronic storage based on the spoken terms and responsive to determination that the spoken terms uttered by second user are the same as the spoken terms included in the library of terms and correlated with the selection sequence; and performing, based on the correlation, the selection sequence correlated with the spoken terms to execute a command and cause the intended result.

14. The method of claim 10, further comprising:

determining frequency of the selection sequence performed by the users subsequent to obtainment of other audio information representing sounds that comprise the spoken terms uttered by other users and subsequent to presentation of the error message, wherein correlating the selection sequence and the terms to generate the correlation is responsive to the frequency meeting a frequency threshold.

15. The method of claim 14, wherein the frequency threshold is definable or fixed.

16. The method of claim 10, wherein the correlating is based on unsupervised clustering.

17. The method of claim 10, wherein the correlating is based on outlier removal.

18. The method of claim 10, wherein the selection sequence represents selections of user interface elements that cause the intended result such that the selection sequence includes selection of a first user interface element, followed by selection of second user interface element, and followed by selection of third user interface element to execute the command, wherein the user interface elements include the first user interface element, the second user interface element, and the third user interface element.

* * * * *